US006833554B2

(12) United States Patent
Wooh (10) Patent No.: US 6,833,554 B2
(45) Date of Patent: Dec. 21, 2004

(54) LASER-INDUCED DEFECT DETECTION SYSTEM AND METHOD

(75) Inventor: Shi-Chang Wooh, Bedford, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/898,815

(22) Filed: Jul. 5, 2001

(65) Prior Publication Data

US 2002/0108445 A1 Aug. 15, 2002

Related U.S. Application Data

(60) Provisional application No. 60/252,368, filed on Nov. 21, 2000.

(51) Int. Cl.$^7$ .............................................. G01N 21/88
(52) U.S. Cl. .......................... 250/559.45; 250/559.42; 356/239.7
(58) Field of Search ....................... 250/559.42, 559.12, 250/559.4, 559.43, 559.44; 356/238.1, 239.4, 239.7, 237.2; 73/655, 657

(56) References Cited

U.S. PATENT DOCUMENTS

| | | | |
|---|---|---|---|
| 3,829,827 A | | 8/1974 | Ernvein |
| 3,978,713 A | | 9/1976 | Penney |
| 4,338,822 A | | 7/1982 | Yamaguchi et al. |
| 4,435,984 A | | 3/1984 | Gruber |
| 4,512,197 A | | 4/1985 | von Gutfeld et al. |
| 4,523,469 A | | 6/1985 | Scott et al. |
| 4,541,280 A | | 9/1985 | Cielo et al. |
| 4,567,769 A | | 2/1986 | Barkhoudarian |
| 5,079,070 A | | 1/1992 | Chalco et al. |
| 5,257,544 A | | 11/1993 | Khuri-Yakub et al. |
| 5,286,313 A | * | 2/1994 | Schultz et al. .............. 148/508 |
| 5,353,512 A | | 10/1994 | Theurer et al. |
| 5,402,235 A | | 3/1995 | Monchalin |

(List continued on next page.)

FOREIGN PATENT DOCUMENTS

WO     WO 99/44029 A1     9/1999

OTHER PUBLICATIONS

U.S. patent application Ser. No. 09/505,039, Wooh, filed Feb. 16, 2000.

Safaeinili et al., "Air–Coupled Ultrasonic Estimation of Viscoelastic Stiffness in Plates",IEEE Transactions on Ultrasonics, Ferroelectrics, and Frequency Control, vol. 43, 1171–1179 (Nov. 1996).

G.A. Alers, *Railroad Rail Flaw Detection System Based on Electromagnetic Acoustic Transducers*, U.S. Department of Transportation Report DOT/FRA/ORD–88/09 (Sep., 1988).

Wooh et al., Time Frequency Analysis of Broadband Dispersive Waves Using the Wavelet Transform, *Review of Progress in Quantitative Nondestructive Evaluations*, American Institute of Physics, Melville, NY, AIP Conference Proceedings, vol. 19A, pp. 831–838, Jul. 25–30, 1999.

C.B.Scruby and L.E. Drain, "Laser–Ultrasonics: Techniques and Applications", Adam Hilger, Briston UK (1990), Ch. 6, pp. 324–405.

*Primary Examiner*—Thanh X. Luu
*Assistant Examiner*—Stephen Yam
(74) *Attorney, Agent, or Firm*—Iandiorio & Teska (57) ABSTRACT

Detecting a defect in the sample is accomplished by photoacousticly exciting acoustic longitudinal, surface Rayleigh, and shear waves at a first point on a near surface of a sample; photoacoustically detecting acoustic waves at a second point spaced from the excitation first point for intercepting shear waves reflected from the far surface of the sample at approximately the angle of maximum shear wave propagation; and detecting the energy level of the intercepted reflected shear waves representative of the flaw in the sample.

19 Claims, 10 Drawing Sheets

U.S. PATENT DOCUMENTS

| | | |
|---|---|---|
| 5,457,997 A | 10/1995 | Naruo et al. |
| 5,549,003 A * | 8/1996 | Drescher-Krasicka ........ 73/606 |
| 5,604,592 A * | 2/1997 | Kotidis et al. .............. 356/493 |
| 5,608,166 A | 3/1997 | Monchalin et al. |
| 5,634,936 A | 6/1997 | Linden et al. |
| 5,684,592 A | 11/1997 | Mitchell et al. |
| 5,698,787 A | 12/1997 | Parzuchowski et al. |
| 5,760,904 A * | 6/1998 | Lorraine et al. ............ 356/513 |
| 5,801,312 A * | 9/1998 | Lorraine et al. .............. 73/602 |
| 6,067,391 A | 5/2000 | Land |
| 6,128,092 A * | 10/2000 | Levesque et al. ........ 356/432 T |
| 6,186,004 B1 | 2/2001 | Kaduchak et al. |
| 6,324,912 B1 | 12/2001 | Wooh |
| 6,351,586 B1 | 2/2002 | Krol et al. |
| 6,360,609 B1 | 3/2002 | Wooh |
| 6,382,028 B1 | 5/2002 | Wooh et al. |
| 2001/0015104 A1 | 8/2001 | Wooh |
| 2001/0020390 A1 | 9/2001 | Wooh |

* cited by examiner

FIG. 11  Diagram for Flaw Detection

LASER-INDUCED DEFECT DETECTION SYSTEM AND METHOD

RELATED APPLICATIONS

This application claims priority of U.S. Provisional Application No. 60/252,368 filed Nov. 21, 2000, entitled NON-CONTACT DETECTION OF RAIL DEFECTS USING LASER-INDUCED ULTRASONIC SHEAR AND SURFACE WAVES.

This work has been sponsored by the Department of Transportation, Federal Railroad Administration under contract DTFRDV-99-G-6007.

FIELD OF THE INVENTION

This invention relates to a system and method for detecting a flaw in a sample and more particularly to such a system and method which distinguishes shear waves from the other acoustic waves to determine the presence and the location, size and orientation of a flaw.

BACKGROUND OF THE INVENTION

Conventional flaw detection systems, particularly those used for examining railroad rails in situ employ a sonic generator such as a piezoelectric ultrasonic transducer in the hub of a wheel that rides on the rail. The acoustic energy is injected into the rail at an angle through the rolling wheel and the backscattered or reflected energy from the flaw is detected either by another transducer or by the same one in pulse echo mode. One shortcoming of this approach is that it requires contact with all the attendant problems of wear, damage, alignment and the inherent limitation on speed. Since these devices require a significant volume it is not always possible to use them to engage the side walls of the rail or sample.

SUMMARY OF THE INVENTION

It is therefore an object of this invention to provide an improved system and method for detecting flaws in a sample.

It is a further object of this invention to provide such a system and method which does not require contact with the sample under examination.

It is a further object of this invention to provide such a system and method which operates in any orientation about the sample.

It is a further object of this invention to provide such a system and method which employs small, compact and light apparatus.

It is a further object of this invention to provide such a system and method which is not inherently limited as to speed.

It is a further object of this invention to provide such a system and method which can determine size, location and orientation of a flaw.

It is a further object of this invention to provide such a system and method which rely on flaw shadows rather than backscattering and so are more sensitive.

It is a further object of this invention to provide such a system and method which can operate remotely from the sample using mirrors or optical fibers.

The invention results from the realization that since shear waves travel a different path and/or have a different velocity than longitudinal and surface Rayleigh waves the presence of a flaw in a sample can be detected by sensing energy levels of the shear waves in a time window that minimizes interference from longitudinal and surface Rayleigh waves, and the further realization that the presence and amplitude of surface Rayleigh waves can be used to normalize the shear wave flaw detection signals and that the shadows of a flaw that indicate the presence of a flaw can be further used to identify the size, location and orientation of that flaw.

This invention features a defect detection system including an excitation laser system for projecting a laser beam at the near surface of the sample to be tested for generating acoustic longitudinal, surface Rayleigh, and shear waves in the sample. A detection laser system spaced from the excitation laser intercepts shear waves reflected from the far surface of the sample at approximately the angle of maximum shear wave propagation. A detection circuit detects the energy level of the reflected shear wave intercepted by the detection laser system representative of a flaw in the sample.

In a preferred embodiment, the excitation laser system and the detection laser system may be on the same side of the sample. There may be a movable support for the excitation laser system and the detection laser system for moving them along the sample. The detection circuit may include a shear wave sensing circuit for sensing the energy level of the acoustic wave at the time of arrival of the reflected shear wave at the detection laser system. A detection circuit may also include a first logic circuit for recognizing the presence of a potential flaw if the energy level of the acoustic wave sensed by the shear wave sensing circuit is less than the predetermined level. The detection circuit may also include a surface Rayleigh wave sensing circuit for sensing the energy level of the acoustic wave at the time of arrival of the surface Rayleigh wave at the detection laser system. There may be a second logic circuit for inhibiting recognition of a potential flaw if the energy level of the acoustic wave sensed by the surface Rayleigh wave sensing circuit is less than the predetermined level and confirming recognition if it is greater than the predetermined level. The detection circuit may include a scanning device for sensing the variation and the energy level of the reflected shear wave along the sample to create shadows of a flaw. A measuring circuit may be used for measuring the length of each shadow cast by a flaw blocking shear wave propagation and the distance between those shadows. A positioning circuit may be used for determining the location, size and orientation of a flaw. The sample may include steel and the angle of maximum shear wave propagation may be approximately 40°.

The invention also features a method of detecting a defect in the sample including photoacoustically exciting acoustic longitudinal surface Rayleigh and shear waves at a first point on the near surface of the sample. Acoustic waves are then detected photoacoustically at a second point spaced from the excitation first point for intercepting shear waves reflected from the far surface of the sample at approximately the angle of maximum shear wave propagation. The energy level of the intercepted reflective shear wave is detected as being representative of a flaw in the sample.

In a preferred embodiment, the excitation and detection may occur on the same side of the sample. The excitation and detection points may be moved along the sample. The energy level of the reflected shear wave may be sensed and the presence of a potential flaw is recognized if the energy level is below a predetermined level. The energy level of the surface Rayleigh waves may be sensed and used to inhibit detection of a flaw if the level of the Rayleigh waves is below a predetermined level. If it is above a predetermined level, it may be used to confirm recognition of a flaw. The variations in energy level of the reflective shear wave along the sample may be used to create shadows of the flaw. The length of each of the shadows cast by the flaw may be measured and then location, size and orientation of the flaw may be determined from the size and the separation of those shadows.

BRIEF DESCRIPTION OF THE DRAWINGS

Other objects, features and advantages will occur to those skilled in the art from the following description of a preferred embodiment and the accompanying drawings, in which.

PREFERRED EMBODIMENT

Figure 1:
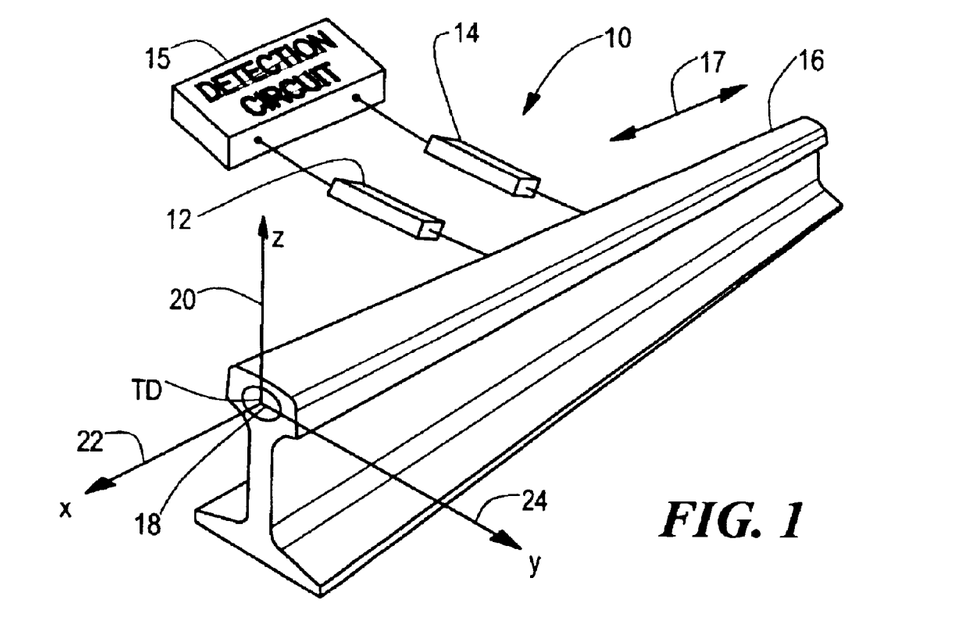
FIG. 1 is a perspective schematic view of a defect detection system according to this invention employed to examine a railway rail.
Figure 2:
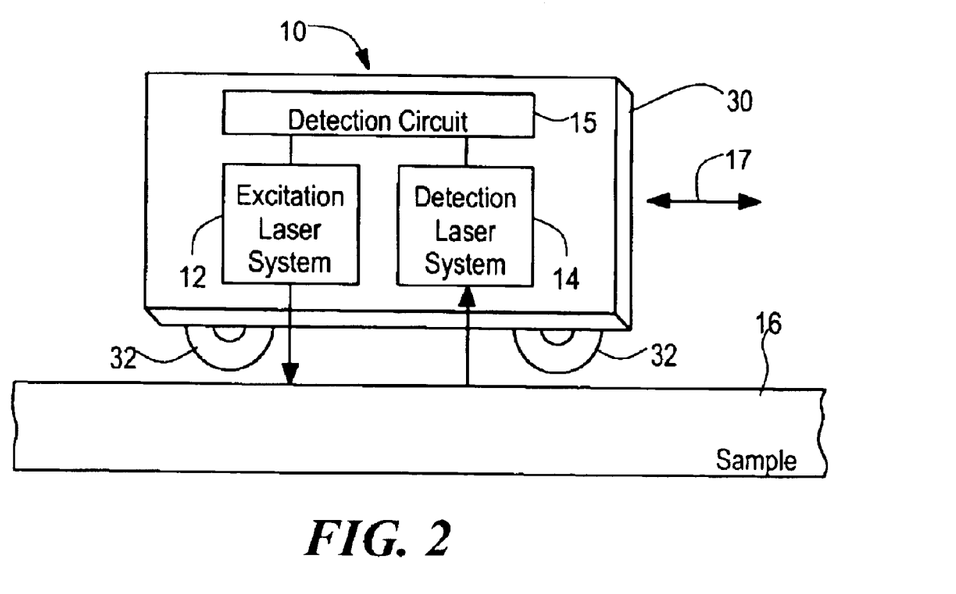
FIG. 2 is a diagrammatic plan view of the system of FIG. 1 mounted on a carriage along side of sample to be examined.

There is shown in FIG. 1 a defect detection system 10 according to this invention including an excitation laser system 12 and detection laser system 14. The sample to be examined in this particular instance includes a railway rail 16 which has a transverse flaw 18 in it. In further discussions herein the z axis 20 is shown generally vertically, the x axis 22 is that which extends longitudinally along rail or sample 16, and the direction y 24 is the transverse direction across the rail. The defect detection system 10, including excitation laser system 12 and detection laser system 14, are generally located on a carriage or vehicle 30, FIG. 2, which moves along, for example, on wheels 32, but may as well be any conventional device. For example, in conjunction with sample 16 being a railway rail as depicted in FIG. 1, vehicle 30 may be a railway vehicle or a special dolly constructed for this purpose as shown in FIG. 2. Detection circuit 15 synchronizes the operation of laser systems 12 and 14, and determines the presence of a flaw as well as its location, size and orientation from the information provided by the sensing of the shear waves.

The entire system 10 may be moved along sample 16 in either direction as indicated by arrows 17. As defect detection system 10 moves along sample 16 excitation laser 12, which may be a Nd:YAG laser provides a beam 40, FIG. 3, that strikes sample 16 and excites acoustic waves including longitudinal and shear waves 44, and surface Rayleigh waves 46. The excitation laser 12 is positioned so that its beam excites the acoustic waves at point A, while detection laser 14 is positioned so that it receives the acoustic waves reflected from far surface 48 and received at point A'. The longitudinal waves travel faster than the shear waves and surface waves so they will arrive at point A' at a different time then the shear waves 44 and surface Rayleigh waves 46. The surface Rayleigh waves 46 and shear waves 44 travel at nearly the same velocity but since the surface waves 46 travel essentially a straight line along the surface from point A to point A' and the shear waves 44 are reflected off the far surface 48 and then returned to point A' they travel a longer distance and so reach point A' at a later time than the surface waves 46.

Figure 3:
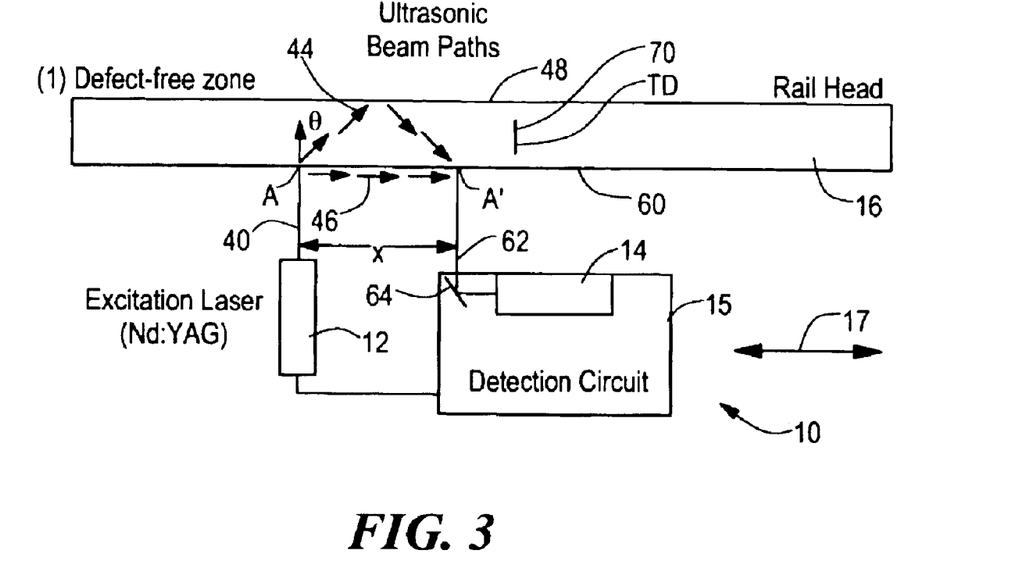
FIG. 3 is a schematic top plan view illustrating the acoustic waves propagating in the sample in accordance with this invention.
Figure 5:
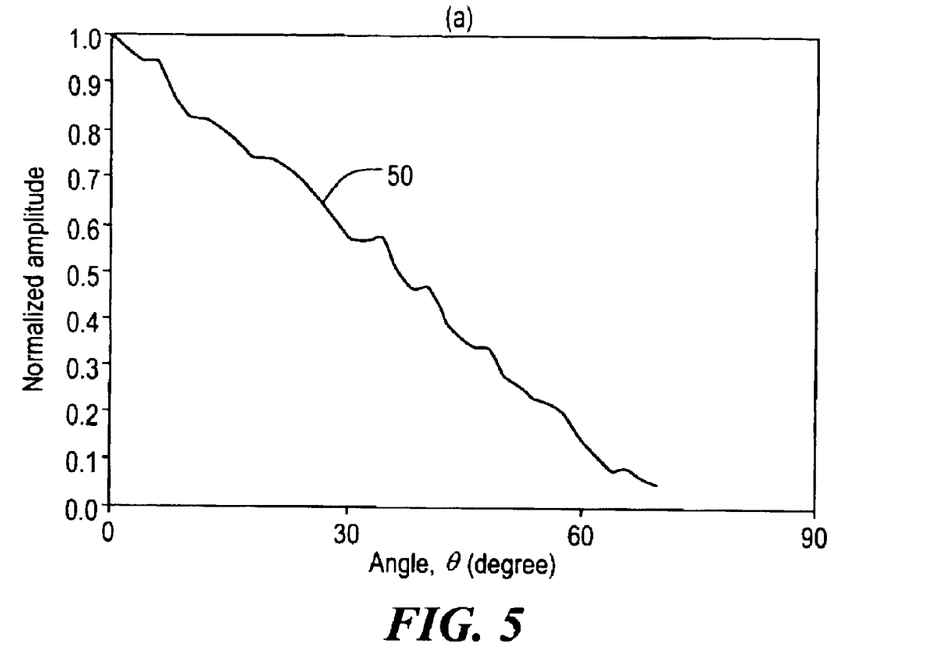
FIG. 5 is an illustration of the variation of the amplitude with respect to propagation angle for longitudinal acoustic waves.
Figure 6:
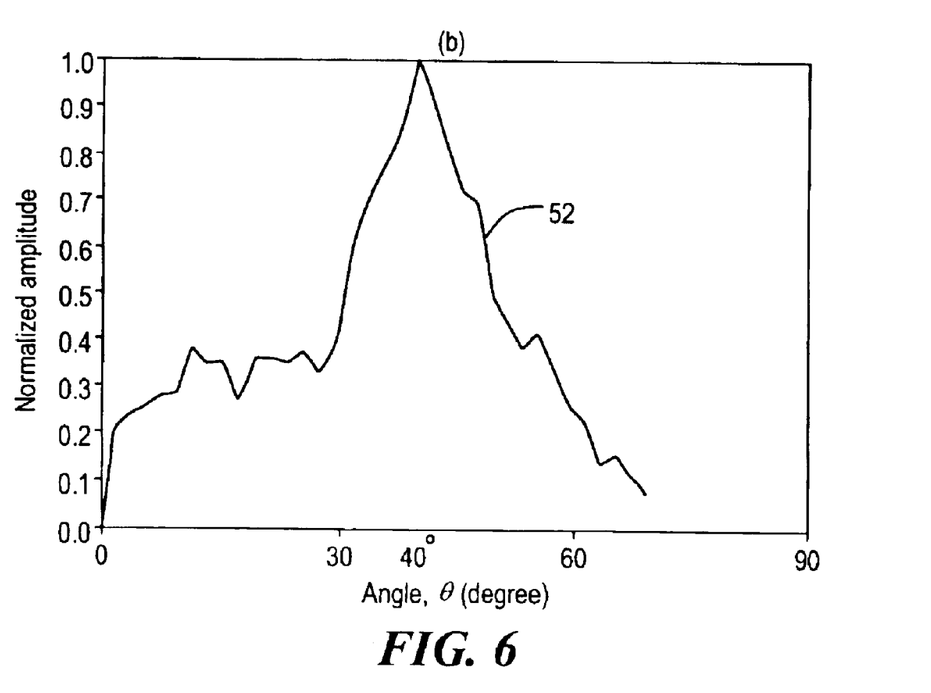
FIG. 6 is an illustration of the variation of the amplitude with respect to propagation angle of acoustic shear waves.

This invention focuses on the detection of the shear waves 44 as distinguished from the surface waves 46 and longitudinal waves 44 that arrive at different times. This invention appreciates that the angle of maximum propagation for longitudinal waves as shown by the characteristic 50, FIG. 5, decreases with increasing angle so that by approximately 70° the amplitude of the longitudinal wave is negligible. In contrast, as shown in FIG. 6 by characteristic 52, shear wave has its maximum propagation at approximately 40°. Thus, the distance x between point A and point A' in FIG. 3 is set so that the angle θ in FIG. 3 is approximately 40°, thus, maximizing the shear wave amplitude at point A' while reducing that of the surface and longitudinal waves. This angle θ varies with the type of material being used. 40° is optimum when the sample 16 is a steel rail; for other materials other angles will be optimum. To calculate this angle θ for a circular source one can employ the formula:

$$H_a^T(\theta) = \begin{cases} \dfrac{J_1(\xi_T)}{\xi_T} H_0^T(\theta), & \text{Dry surface} \\ \dfrac{J_2(\xi_T)}{\xi_T^2} H_0^T(\theta), & \text{Wet surface} \end{cases} \quad (1)$$

There are actually two formulas given, one for a dry surface and one for a wet surface as it has been observed on some occasions that a fairly intense excitation laser beam is preferable. To prevent any overheating from such an intense beam the surface may be cooled such as by wetting with a water spray. In equations (1) $J_1$ and $J_2$ are the Bessel functions of the first and second kinds.

$H_o^T$ is defined in equation (2):

$$H_o^T(\theta) = \frac{(k_T^2\sin^2\theta - k_L^2)^{1/2}\sin 2\theta}{G(k_T\sin\theta)} \quad (2)$$

$\xi_L$ and $\xi_T$ are defined in equations (3) and (4):

$$\xi_L = k_L a \sin\theta \quad (3)$$

$$\xi_T = k_T a \sin\theta \quad (4)$$

where $k_T$, $k_L$ are the wave numbers and $G(\zeta)$ is determined as in equation (5):

$$G(\zeta) = (2\zeta^2 - k_T^2)^2 - 4\zeta^2$$

$$\sqrt{(\zeta^2-k_{L^2})(\zeta^2-k_T^2)} \quad (5)$$

$H_o^T(\theta)$ is the far-field directivity of point or hairline sources ($a \to 0$).

For line focus sources equation (6) expresses the directivities.

$$H_{la}^T(\theta) \begin{cases} \dfrac{\sin(\xi_T)}{\xi_T} H_0^T(\theta), & \text{Dry surface} \\ \dfrac{1}{\xi_T^2}\left(\dfrac{\sin(\xi_T)}{\xi_T} - \cos(\xi_T)\right) H_0^T(\theta) & \text{Wet surface} \end{cases} \quad (6)$$

Figure 4:
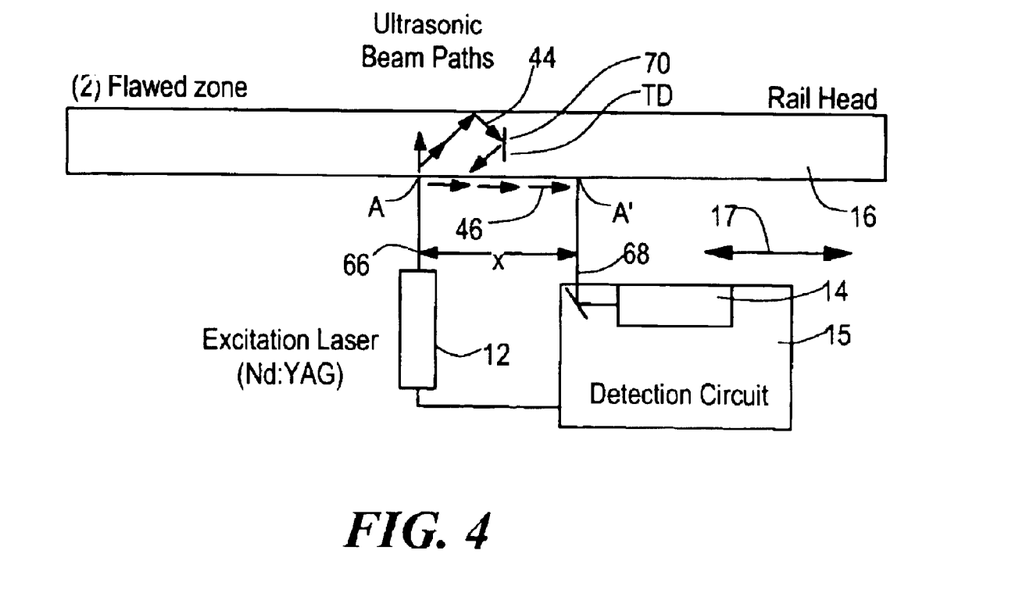
FIG. 4 is a view similar to FIG. 3 when the defect detection system according to this invention has encountered a flaw in the sample.

Both the excitation laser 12 and the detection laser 14 may be on the same side of sample 16 such as the near side 60, FIG. 3, or one could be on the near side 60 and one may be on the far side 48. Detection laser 14 may be an interferometer type or photo-EMF such as provided by Lasson Technologies, Inc., while the excitation laser beam 40 and the return beam 62 are shown as free-space beams wherein beam 62 employs a mirror 64, for example. This is not a necessary limitation in the invention, for example as shown in FIG. 4 excitation laser 12 and detection laser 14 may use optical fibers 66 and 68, so that they may be as large and as remote as desired and still provide the necessary proximity to sample 16.

In FIG. 3 sample 16 contains a transverse flaw 70 which has not yet been encountered by the field of the acoustic waves of the traveling defect detection system 10. In FIG. 4 this has occurred and now the T-waves 44 are blocked by the flaw 70 and reflected backward towards point A; they do not reach point A'. Surface waves 46 do reach point A'.

Figure 7:
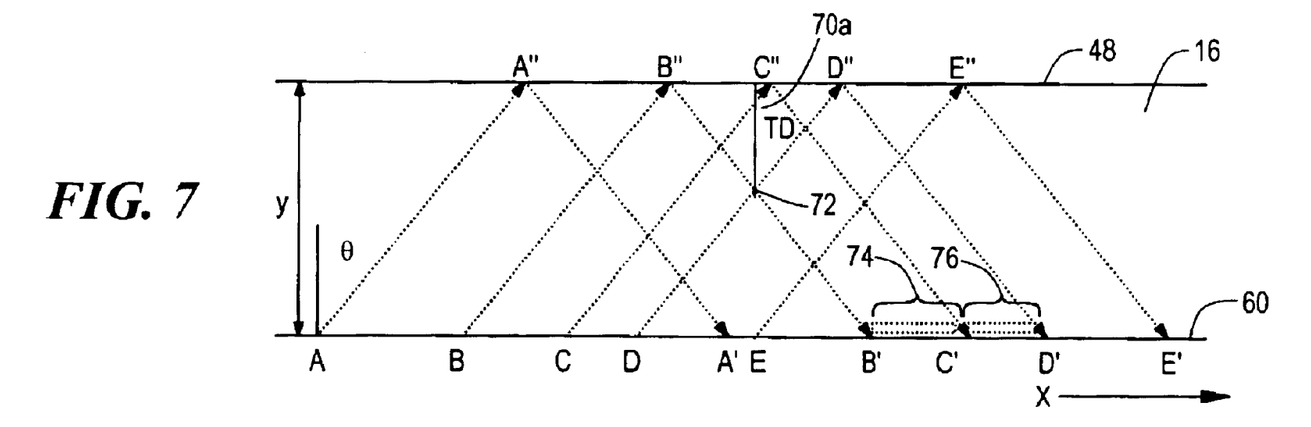
FIG. 7 is a diagrammatic view showing the interaction of the shear waves with a transverse flaw against the far surface of the rail sample as the exciting laser and detecting laser move along the sample creating shadows of the flaw.

The operation of the defect detection system is shown in greater detail in FIG. 7 where the sample 16 is shown in diagrammatic form with a transverse flaw located against the far surface 48 of the sample. Both the excitation laser 12 and detection laser 14 are located on the near surface 60 of sample 16, but are not shown in FIG. 7. Instead the successive points of excitation are shown as A, B, C, D, and E and the points where the reflected shear wave is detected are indicated by points A', B', C', D', and E'. The rays reflect off the far surface 48 at points A", B", C", D" and E". The angle θ is also depicted as are directions x and y established in FIG. 1. Thus, the shear wave moving from point A" back to A' does not encounter flaw 70a. Shear wave B does encounter just the tip 72 of flaw 70a. This is the beginning or the boundary of shadow 74. Subsequent rays are blocked by flaw 70a creating shadow 74 and shadow 76. The original rays of those that run from the unprimed letters A, B, C, D, E to the double primes, A", B", C", D", E" whereas the reflected rays are those running from the double prime letters to the single prime letters A', B', C', D', and E'.

Figure 8A:
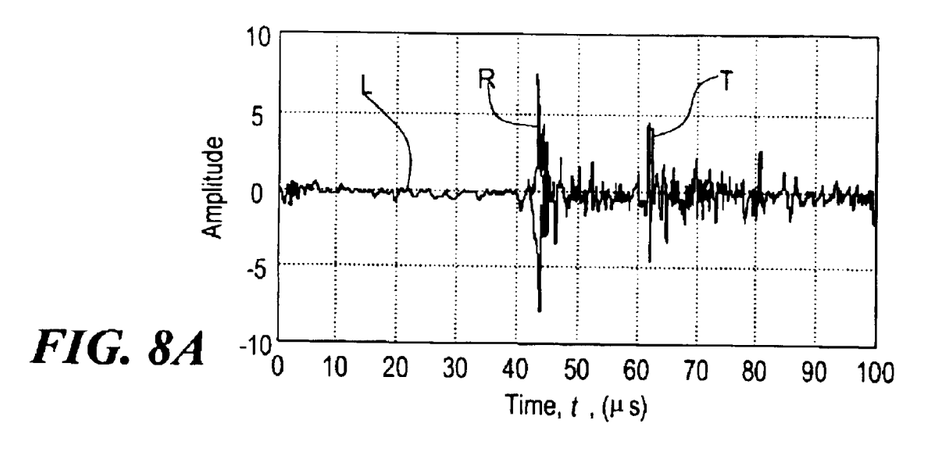
FIGS. 8A–E illustrate waveforms representing the amplitude of the longitudinal, surface and shear waves with respect to time as the defect detection system moves along the sample from point A to point E and A' to E'.
Figure 8B:
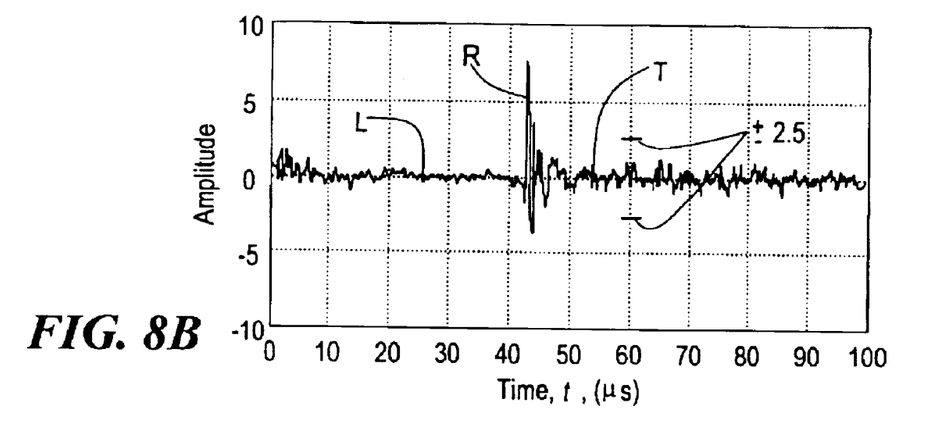
Figure 8C:
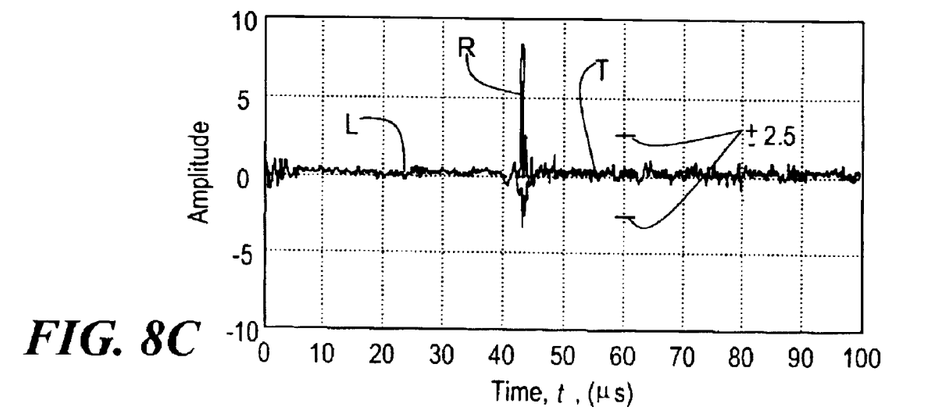
Figure 8D:
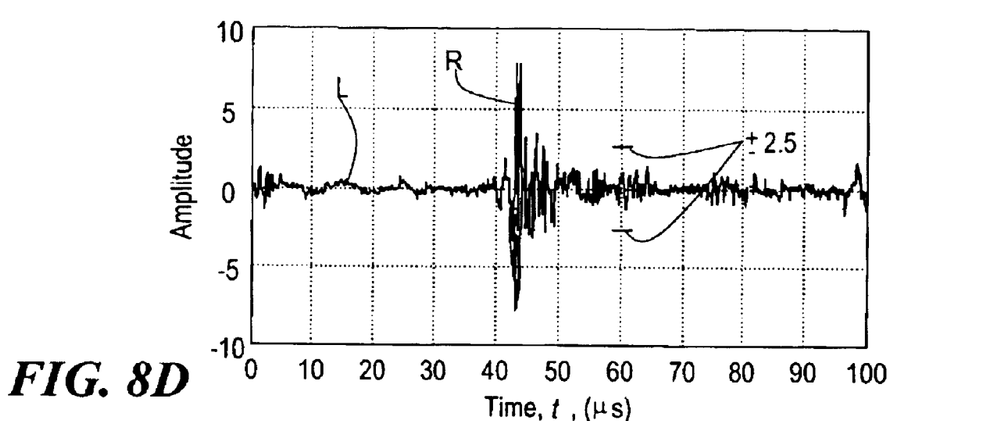
Figure 8E:
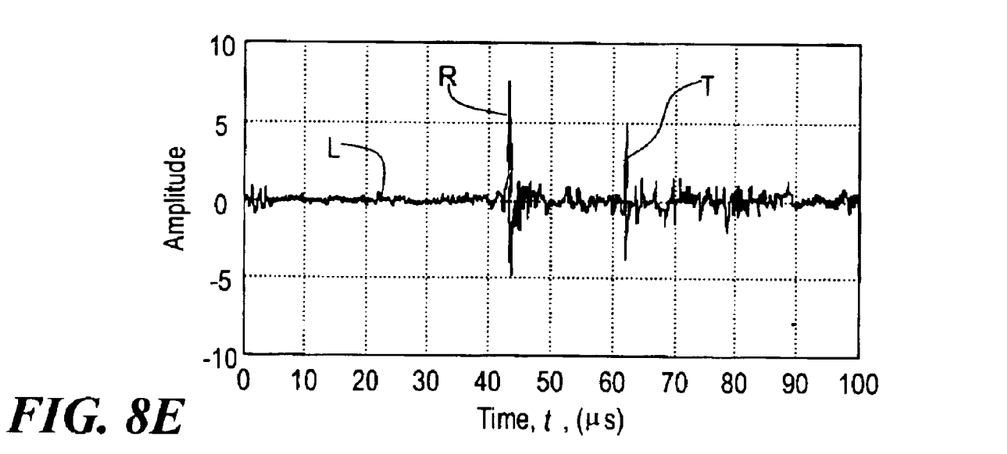

The form of the acoustic waves being detected at points A', B', C', D', and E' are shown, respectively, in the waveforms of FIG. 8A, FIG. 8B, FIG. 8C, FIG. 8D, and FIG. 8E. At point A', FIG. 8A, the longitudinal wave L and surface wave R arrive earlier than the transverse shear wave T which has a substantial amplitude but not as great as the surface wave R. At point B', FIG. 8B, a reflective wave from point B" has encountered the tip 72 of flaw 70a; the amplitude of the T-wave is severely reduced while the L-wave and R-wave remain similar to their previous state. The same case is true in FIG. 8C, depicting the condition at C", and at D" as depicted in FIG. 8D. At E" where the shear wave is once again free of interference from the flaw 70a, the T-wave is once again fairly large. By setting a gate which is tripped when the T-wave is below some predetermined level, for example the normal amplitude +2.5 in FIGS. 8B, 8C and 8D, the presence of the flaw can be detected.

Figure 9:
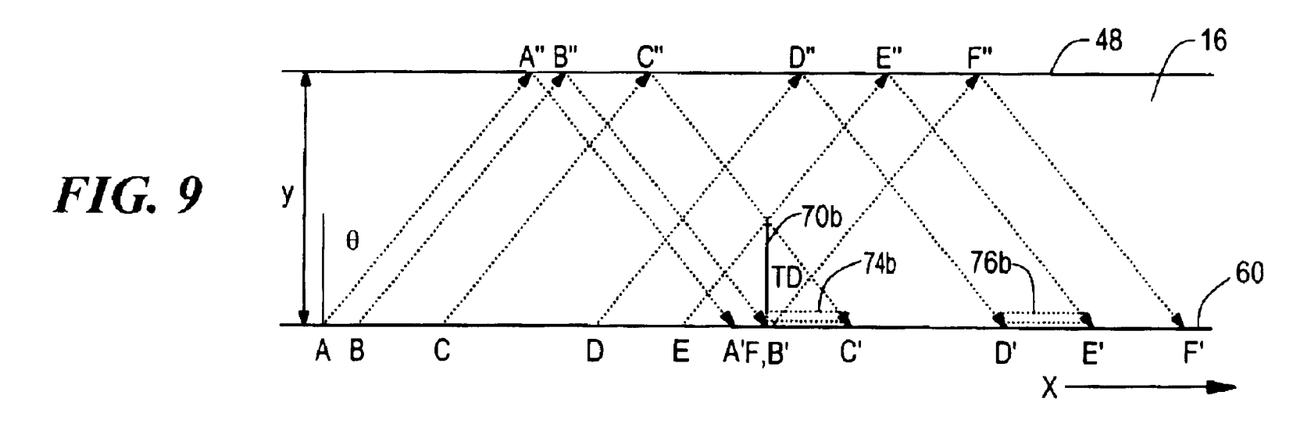
FIG. 9 is a view similar to FIG. 7 with the flaw against the near wall.
Figure 10:
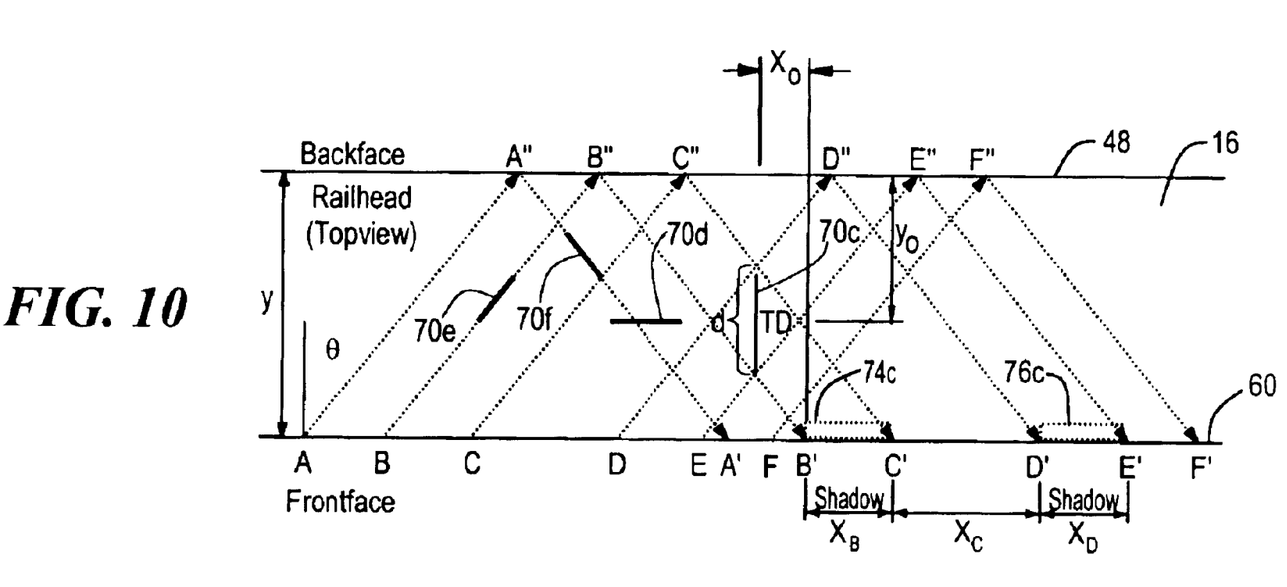
FIG. 10 is a view similar to FIG. 7 with the flaw in the middle.

A separation and the position of the shadows 74 and 76 varies as a function of the position of the flaw, thus in FIG. 9 where the flaw 70b is against the near surface 60 of sample 16 the two shadows 74b and 76b are separated rather than adjacent as in FIG. 7. When the flaw 70c, FIG. 10 is more in the center of sample 16 shadows 74c and 76c are still separated but by a lesser amount. The size of the shadows 74, and 76 are indicated in FIG. 10 as $x_B$ and $x_D$. The distance between them is indicated as $x_C$. The sizes $x_B$, $x_D$ and the distance between the shadows $x_C$ may be used to calculate the location and size and even the orientation of the flaw. Although thus far the flaws are always shown as virtually transverse in the sample, this is not a necessary limitation of the invention. Because of the paths of the original and reflected shear waves it makes no difference whether the flaw is transverse as shown in 70c, or parallel as shown at 70d, or at an angle in either direction as shown at 70e and 70f: in all cases the flaw will still block or intercept various ones of the original and reflected shear waves thereby creating the shadows and establishing a distance between them from which the calculations can be made. For a transverse defect for example, the location of the flaw can be calculated from the equation(s):

$$x_0 = h\tan\theta - \frac{3x_B + 2x_C + x_D}{4} \quad (7)$$

$$y_0 = \frac{x_B + 2x_C + x_D}{4\tan\theta}$$

the size of the flaw can be determined in accordance with the equation(s):

$$d = \frac{x_B + x_D}{2\tan\theta} \quad (8)$$

Figure 11:
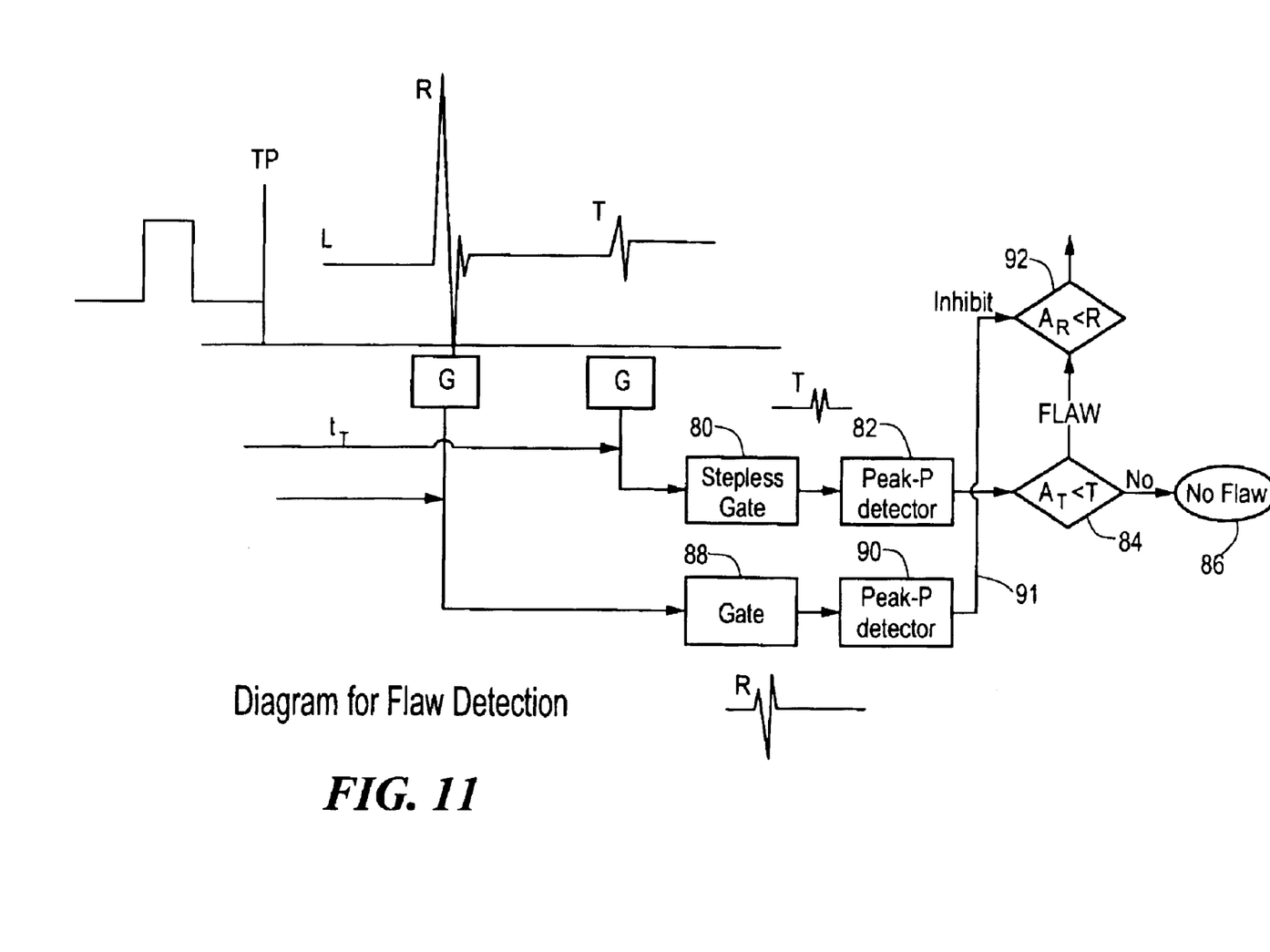
FIG. 11 is a schematic block diagram of a detection circuit for determining the presence or absence of a flaw.

In accordance with this invention the flaws can be detected using a first gate 80, FIG. 11, which is operated at the time window when the shear wave T is expected. The sensed signal at that point is delivered to peak detector 82 which determines the amplitude of the shear wave gated through by gate 80. If the amplitude $A_T$ of the shear wave amplitude is less than a predetermined level T then the logic 84 determines that there may indeed be a flaw. If the amplitude $A_T$ is greater than the predetermined amplitude, then it is determined that no flaw 86 is present. In a further implementation it may be desirable to guard against the fluctuation and signal levels which may give rise to a detection of a flaw when there in fact is none simply because the entire signal decreased and so while the amplitude $A_T$ of the shear wave is indeed less than the threshold predetermined value T it is not indicative of a flaw, only the result of an overall decrease in signal strength. To accommodate for this the surface wave R may be gated through the time window for the R-wave through gate 88 to peak detector 90. If the peak detected is less than a predetermined threshold an inhibit signal is delivered on line 91. If the value $A_R$ of the R-wave is less than predetermined level R, then the logic at 92 will override or inhibit the indication of a flaw from circuit 84 and indicate no defect. The time windows for the shear wave T and surface wave R may be calculated in accordance with the equations (9) and (10), respectively, where x is the distance between the two laser beam spots, h is the width of the sample in the y direction, and $c_T$ and $c_R$ are the wave speeds of the T and R-waves, respectively.

$$t_T = \frac{\sqrt{x^2 + 4h^2}}{c_T} \quad (9)$$

$$t_R = \frac{x}{c_R} \quad (10)$$

Figure 12:
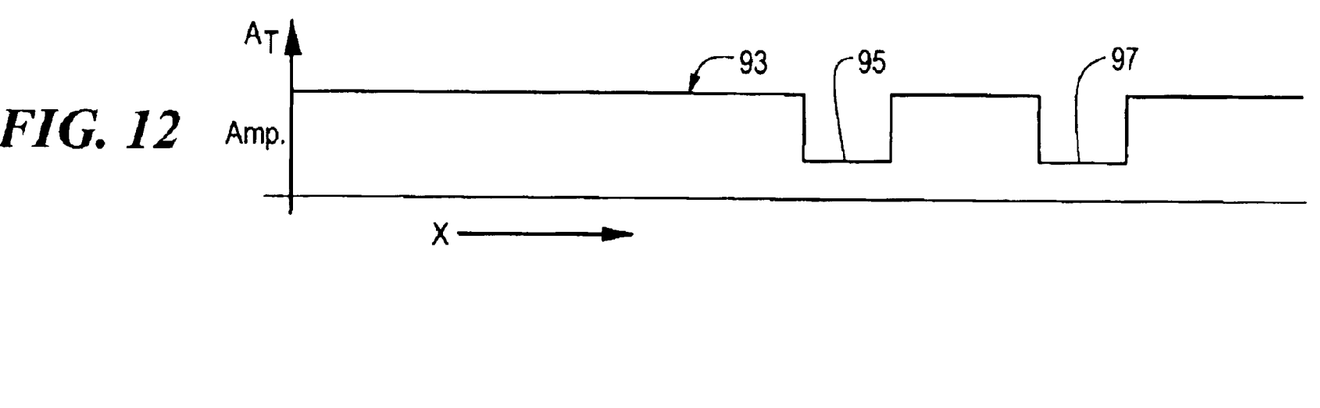
FIG. 12 illustrates a waveform of amplitude over distance along a sample.
Figure 13:
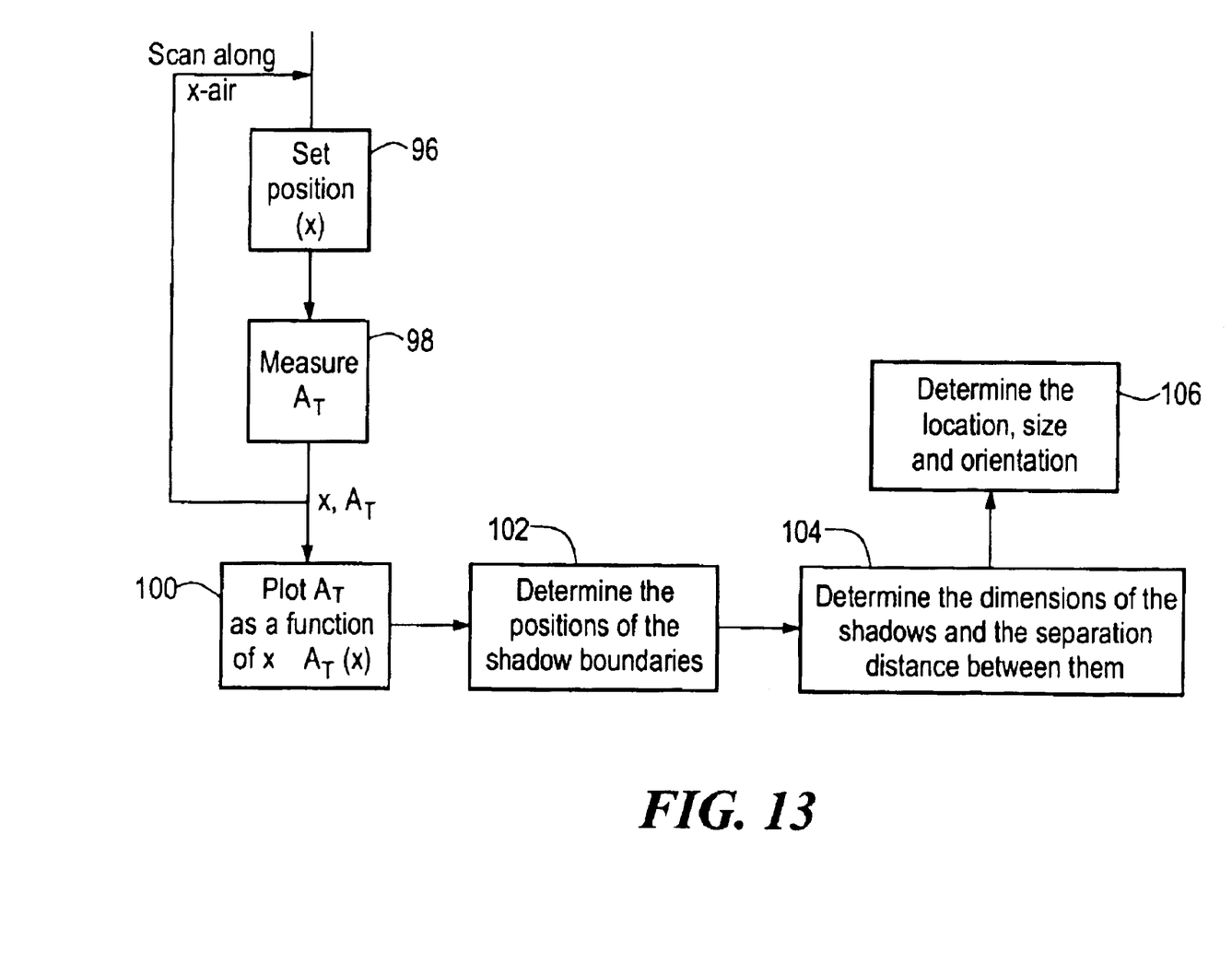
FIG. 13 is a schematic block diagram of a positioning circuit for determining the location, size and orientation of a detected flaw.

For the flaw angle equal to zero, the location and size of the flaw can be determined from the size of the shadows $x_B$, $x_D$ and their separation $x_C$. This is done by simply scanning along the x axis to determine the amplitude $A_T$ of the T wave as indicated by characteristic 93 in FIG. 12. This amplitude drops at 95 associated with shadow 74c, FIG. 10, and at 97 associated with shadow 76c, FIG. 10. Thus, by scanning along the x axis along set positions as indicated at 96, FIG. 13, and measuring the amplitude of the T wave $A_T$ at each point, the information concerning the amplitude at each position $A_T$ as a function of x can be plotted, stored or otherwise used 100 to determine the positions of the shadow boundaries 102. From this the dimensions of the shadows and their separation distance is determined 104. Afterwards the location, the size and the orientation can be determined 106.

Figure 14:
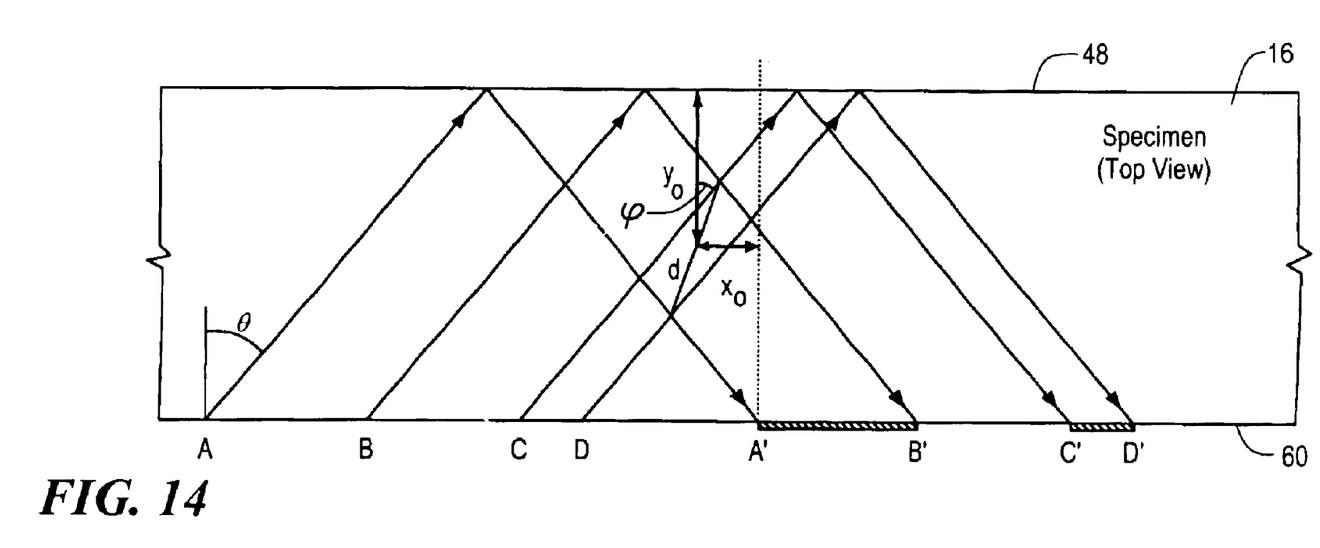
FIG. 14 is a view similar to FIG. 7 with a flaw at an angled orientation.
Figure 15:
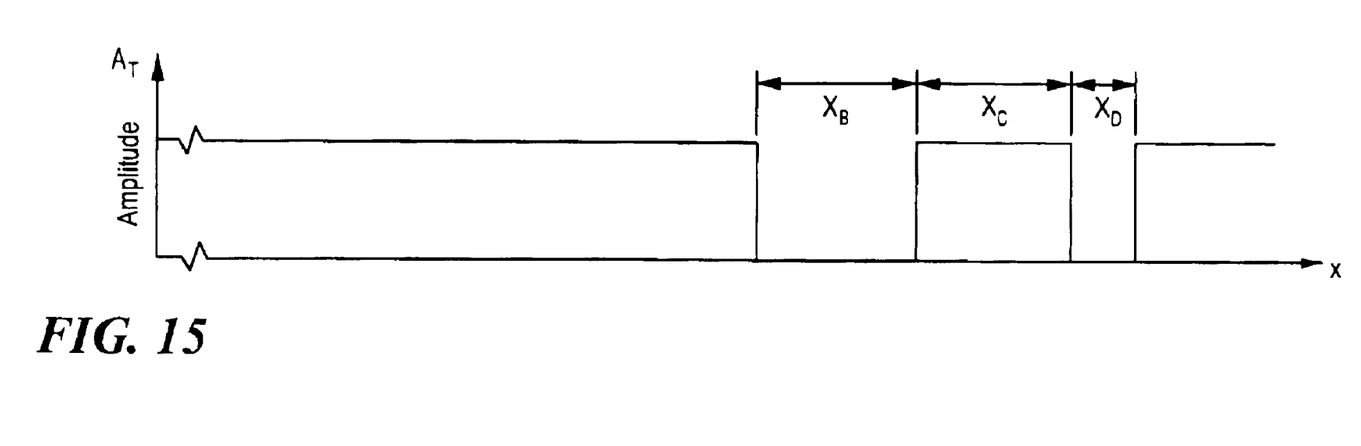
FIG. 15 illustrates a waveform of amplitude over distance along the sample of FIG. 14.

From the geometrical relations, as shown in FIGS. 11 and 14 the following equations may be derived for characterizing the flaw by determining all the parameters: location ($x_0$, $y_0$), length d, and orientation $\phi$.

The locations can always be found from the relation:

$$x_0 = h\tan\theta - \frac{3x_B + 2x_C + x_D}{4} \quad (11)$$

$$y_0 = \frac{x_B + 2x_C + x_D}{4\tan\theta} \quad (12)$$

But unfortunately it is not possible to measure the flaw size and orientation from a single measurement. They could be either one of the following values:

If $|\varphi| < \theta$, $$d = \frac{1}{2}\sqrt{\left(\frac{x_B + x_D}{\tan\theta}\right)^2 + (x_B - x_D)^2} \quad (13)$$

$$\tan\varphi = \frac{x_B - x_D}{x_B + x_D}\tan\theta \quad (14)$$

$$(15)$$

If $0° < \theta \le |\varphi| < 90°$, $$d = \frac{1}{2}\sqrt{\left(\frac{x_B + x_D}{\tan\theta}\right)^2 + (x_B + x_D)^2} \quad (16)$$

$$\tan\varphi = \frac{x_B + x_D}{x_B - x_D}\tan\theta \quad (17)$$

$$(18)$$

For a special angle $\theta$ of 45 degree, it is possible to determine the flaw from the relation:

$$d = \frac{1}{2}\sqrt{2x_B^2 + 2x_D^2} \quad (19)$$

but the angle is still not determined. It is one of the following values:

$$\tan\varphi = \frac{x_B - x_D}{x_B + x_D} \quad \text{or} \quad \tan\varphi = \frac{x_B + x_D}{x_B - x_D} \quad (20)$$

To solve this problem, dual detection probes may be used. The detection probes may be placed at a distance to pick up the signals at two different propagation angles. Since the flaw angle should be independent of the propagation angle, there should be two common values obtained from the dual measurements. The angle may be obtained by choosing the common value.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. A defect detection system comprising:
   an excitation laser system for projecting a laser beam at the near surface of a sample to be tested for generating acoustic longitudinal, surface Rayleigh, and shear waves in the sample;
   a detection laser system spaced from said excitation laser for projecting a laser beam and to intercept shear waves reflected from the far surface of the sample at approximately the angle of maximum shear wave propagation and minimize interference with longitudinal and surface Rayleigh waves; and
   a detection circuit for detecting the energy level of the reflected shear wave intercepted by said detection laser system representative of a flaw in the sample.

2. The defect detection system of claim 1 in which the excitation laser system and detection laser system are on the same side of the sample.

3. The defect detection system of claim 1 including a movable support for said excitation laser system and detection laser system for moving them along the sample.

4. The defect detection system of claim 1 in which said detection circuit includes a shear wave sensing circuit for sensing the energy level of the reflected shear waves and the time of arrival of the reflected shear wave at the detection laser system.

5. The defect detection system of claim 4 in which said detection circuit includes a first logic circuit for recognizing the presence of a potential flaw if the energy level of the reflected shear waves sensed by said shear wave sensing circuit is less than a predetermined level.

6. The defect detection system of claim 5 in which said detection circuit includes a surface Rayleigh wave sensing circuit for sensing the energy level of the surface Rayleigh waves at the time of arrival of the surface Rayleigh wave at the detection laser system.

7. The defect detection system of claim 6 in which said detection circuit includes a second logic circuit for inhibiting recognition of a potential flaw if the energy level of the surface Rayleigh waves sensed by said surface Rayleigh wave sensing circuit is less than a predetermined level and confirming recognition if it is greater than the predetermined level.

8. The defect detection system of claim 1 in which said detection circuit includes a scanning device for sensing the variation in the energy level of the reflected shear wave along the sample to create shadows of a flaw.

9. The defect detection system of claim 8 in which said detection circuit includes a measuring circuit for measuring the length of each shadow cast by a flaw blocking shear wave propagation and the distance between those shadows.

10. The defect detection system of claim 9 including a positioning circuit for determining the location, size and orientation of a flaw.

11. The defect detection system of claim 1 in which the sample includes steel and the angle of maximum shear wave propagation is approximately 40°.

12. A method of detecting a defect in a sample comprising:

photoacoustically exciting acoustic longitudinal, surface Rayleigh, and shear waves with an excitation laser beam at a first point on the near surface of the sample;

photoacoustically detecting acoustic waves with a detection laser beam at a second point spaced from the excitation first point for intercepting shear waves reflected from the far surface of the sample at approximately the angle of maximum shear wave propagation and minimizing interference with longitudinal and surface Rayleigh waves; and detecting the energy level of the intercepted reflected shear wave representations of a flaw in the sample.

13. The method of claim 12 in which the excitation and detection occurs on the same side of the sample.

14. The method of claim 12 in which the excitation and detection points are moved along the sample.

15. The method of claim 12 further including sensing the energy level of the reflected shear wave and recognizing the presence of a potential flaw if the energy level is below a predetermined level.

16. The method of claim 12 further including sensing the energy level of the surface Rayleigh waves and inhibiting detection of a flaw if that level is below a predetermined level and confirming recognition if it is greater than the predetermined level.

17. The method of claim 12 further determining the variation in energy level of the reflected shear wave along the sample to create shadows of the flaw.

18. The method of claim 17 further including measuring the length of each shadow cast by the flaw.

19. The method of claim 18 further including determining the location, size and orientation of a flaw from the size and separation of the shadows.

\* \* \* \* \*